United States Patent [19]

Rohrbach et al.

[11] 4,206,259

[45] Jun. 3, 1980

[54] SUPPORT MATRICES FOR IMMOBILIZED ENZYMES

[75] Inventors: Ronald P. Rohrbach, Forest Lake, Ill.; Joseph Levy, Deerfield Beach, Fla.

[73] Assignee: UOP Inc., Des Plaines, Ill.

[21] Appl. No.: 951,949

[22] Filed: Oct. 16, 1978

[51] Int. Cl.$^2$ .............................................. B32B 3/26
[52] U.S. Cl. ..................................... 428/304; 435/180
[58] Field of Search .................. 195/63, 68, DIG. 11; 428/304

[56] References Cited

U.S. PATENT DOCUMENTS

| | | | |
|---|---|---|---|
| 3,796,634 | 3/1974 | Haynes et al. | 195/63 |
| 3,850,751 | 11/1974 | Messing | 195/63 |
| 4,048,018 | 9/1977 | Coughlin et al. | 195/63 |
| 4,066,504 | 1/1978 | Krasnobajew et al. | 195/DIG. 11 |

OTHER PUBLICATIONS

*Biotechnology and Bioengineering,* "Enzyme Immobilization on Macroreticular Polystyrene", by George Baum, vol. XVII, pp. 253-270 (1975).

*Primary Examiner*—George F. Lesmes
*Assistant Examiner*—E. Rollins Buffalow
*Attorney, Agent, or Firm*—James R. Hoatson, Jr.; Raymond H. Nelson; William H. Page, II

[57] ABSTRACT

Organic-inorganic support matrices for immobilized enzymes comprise a solid, porous, inorganic, water insoluble support combined with a copolymeric material resulting from the reaction of aminopolystyrene and a bifunctional monomer. The matrix is prepared by depositing a salt of amino-polystyrene within the pores of the solid support from an aqueous solution at a pH less than 7 after which the resulting composite is then reacted with an excess of a bifunctional reactive monomer thus forming a copolymeric organic material in situ substantially entrapped in the pores of the support and containing functionalized pendent groups to which an enzyme may be coupled to form an immobilized enzyme conjugate.

12 Claims, No Drawings

SUPPORT MATRICES FOR IMMOBILIZED ENZYMES

BACKGROUND OF THE INVENTION

It is known that enzymes, which are proteinaceous in nature and which are commonly water soluble, comprise biological catalysts which serve to regulate many and varied chemical reactions which occur in living organisms. The enzymes may also be isolated and used in analytical, medical and industrial applications. For example, they find use in industrial applications in the preparation of food products such as cheese or bread as well as being used in the preparation of alcoholic beverages. Some specific uses in industry may be found in the use of enzymes such as in the resolution of amino acids; in the modification of penicillin to form various substrates thereof; the use of various proteases in cheese making, meat tenderizing, detergent formulations, leather manufacture and as digestive aids; the use of carbohydrases in starch hydrolysis, sucrose inversion, glucose isomerization, etc.; the use of nucleases in flavor control; or the use of oxidases in oxidation prevention and in the color control of food products. These uses as well as many others have been well delineated in the literature.

As hereinbefore set forth, inasmuch as enzymes are commonly water soluble as well as being generally unstable and readily deactivated, they are also difficult either to remove from the solutions in which they are utilized for subsequent reuse or it is difficult to maintain their catalytic activity for a relatively extended period of time. The aforementioned difficulties will, of course, lead to an increase cost in the use of enzymes for commercial purposes due to the necessity for frequent replacement of the enzyme, this replacement being usually necessary with each application. To counteract the high cost of replacement, it has been suggested to immobilize or insolubilize the enzymes prior to the use thereof. By immobilizing the enzymes through various systems hereinafter set forth in greater detail, it is possible to stabilize the enzymes in a relative manner and, therefore, to permit the reuse of the enzyme which may otherwise undergo deactivation or be lost in the reaction medium. Such immobilized or insolubilized enzymes may be employed in various reactor systems such as in packed columns, stirred tank reactors, etc., depending upon the nature of the substrate which is utilized therein. In general, the immobilization of the enzymes provides a more favorable or broader environmental and structural stability, a minimum of effluent problems and materials handling as well as the possibility of upgrading the activity of the enzyme itself.

As hereinbefore set forth, several general methods, as well as many modifications thereof, have been described by which the immobilization of enzymes may be effected. One general method is to adsorb the enzyme at a solid surface as, for example, when an enzyme such as amino acid acylase is adsorbed on a cellulosic derivative such as DEAE-cellulose; papain or ribonuclease is adsorbed on porous glass; catalase is adsorbed on charcoal; trypsin is adsorbed on quartz glass or cellulose, chymotrypsin is adsorbed on kaolinite, etc. Another general method is to trap an enzyme in a gel lattice such as glucose oxidase, urease, papain, etc., being entrapped in a polyacrylamide gel; acetyl cholinesterase being entrapped in a starch gel or a silicone polymer; glutamic-pyruvic transaminase being entrapped in a polyamide or cellulose acetate gel, etc. A further general method is a cross-linking by means of bifunctional reagents and may be effected in combination with either of the aforementioned general methods of immobilization. When utilizing this method, bifunctional or polyfunctional reagents which may induce intermolecular cross-linking will covalently bind the enzymes to each other as well as on a solid support. This method may be exemplified by the use of glutaraldehyde or bisdiazobenzidine-2,2'-disulfonic acid to bind an enzyme such as papain on a solid support, etc. A still further method of immobilizing an enzyme comprises the method of a covalent binding in which enzymes such as glucoamylase, trypsin, papain, pronase, amylase, glucose oxidase, pepsin, rennin, fungal protease, lactase, etc., are immobilized by covalent attachment to a polymeric material which is attached by various means to an organic or inorganic solid porous support. This method may also be combined with the aforesaid immobilization procedures.

The above enumerated methods of immobilizing enzymes all possess some drawbacks which detract from their use in industrial processes. For example, when an enzyme is directly adsorbed on the surface of a support, the binding forces which result between the enzyme and the carrier support are often quite weak, although some prior art has indicated that relatively stable conjugates of this type have been obtained when the pore size of the support and the spin diameter of the enzyme are correlated. However, in such cases it is specified that the pore size of the support cannot exceed a diameter of about 1000 Angstroms. In view of this weak bond, the enzyme is often readily desorbed in the presence of solutions of the substrate being processed. In addition to this, the enzyme may be partially or extensively deactivated due to its lack of mobility or due to interaction between the support and the active site of the enzyme. Another process which may be employed is the entrapment of enzymes in gel lattices which can be effected by polymerizing an aqueous solution or emulsion containing the monomeric form of the polymer and the enzyme or by incorporating the enzyme into the preformed polymer by various techniques, often in the presence of a cross-linking agent. While this method of immobilizing enzymes has an advantage in that the reaction conditions utilized to effect the entrapment are usually mild so that often there is little alteration or deactivation of the enzyme, it also has disadvantages in that the conjugate has poor mechanical strength, which results in compacting when used in columns in continuous flow systems, with a concomitant plugging of the column. Such systems also have rather wide variations in pore size thus leading to some pore sizes which are large enough to permit the loss of enzyme. In addition, some pore sizes may be sufficiently small so that large diffusional barriers to the transport of the substrate and product will lead to reaction retardation, this being especially true when using a high molecular weight substrate. The disadvantages which are present when immobilizing an enzyme by intermolecular cross-linkage, as already noted, are due to the lack of mobility with resulting deactivation because of inability of the enzyme to assume the natural configuration necessary for maximum activity, particularly when the active site is involved in the binding process.

Covalent binding methods have found wide applications and may be used either as the sole immobilization technique or as an integral part of many of the methods already described in which cross-linking reactions are employed. This method is often used to bind the enzyme as well as the support through a bifunctional intermediary molecule in which the functional groups of the molecule, such as, for example, gamma-aminopropyltriethoxysilane, are capable of reacting with functional moieties present in both the enzyme and either an organic or inorganic porous support. A wide variety of reagents and supports has been employed in this manner and the method has the advantage of providing strong covalent bonds throughout the conjugate product as well as great activity in many cases. The covalent linkage of the enzyme to the carrier must be accomplished through functional groups on the enzyme which are non-essential for its catalytic activity such as free amino groups, carboxyl groups, hydroxyl groups, phenolic groups, sulfhydryl groups, etc. These functional groups will also react with a wide variety of other functional groups such as an aldehydo, isocyanato, acyl, diazo, azido, anhydro activated ester, etc., to produce covalent bonds. Nevertheless, this method also often has many disadvantages involving costly reactants and solvents, as well as specialized and costly porous supports and cumbersome multi-step procedures, which render the method of preparation uneconomical for commercial application.

The prior art is therefore replete with various methods for immobilizing enzymes which, however, in various ways fail to meet the requirements of economical industrial use. However, as will hereinafter be discussed in greater detail, none of the prior art compositions comprise the composition of matter of the present invention which constitutes an inorganic porous support containing a copolymer, formed in situ from a polyfunctional monomer, a low molecular weight polymer, a polymer hydrolysate, or a preformed polymer, of natural or synthetic origin by reaction with a bifunctional monomer, the copolymer formed being substantially entrapped within the pores of said support, and which contains terminally functionalized, pendent groups extending therefrom; the enzyme being covalently bound to the active moieties at the terminal reactive portions of the pendent groups, thus permitting the freedom of movement which will enable the enzyme to exercise maximum activity. A variable portion of the enzyme will also be adsorbed upon the matrix, but this will be recognized as an unavoidable consequence of almost all immobilization procedures involving porous inorganic supports and is not to be considered a crucial aspect of this invention. Furthermore, the bond between the inorganic support and the organic copolymer which has been prepared in situ in the pores of the support is not covalent but rather physico-chemical and mechanical in nature and the inorganic-organic matrix so produced presents high stability and resistance to disruption. As further examples of prior art, U.S. Pat. No. 3,556,945 relates to enzyme composites in which the enzyme is adsorbed directly to an inorganic carrier such as glass. U.S. Pat. No. 3,519,538 is concerned with enzyme composites in which the enzymes are chemically coupled by means of an intermediary silane coupling agent to an inorganic carrier. In similar fashion, U.S. Pat. No. 3,783,101 also utilizes an organosilane composite as a binding agent, the enzyme being covalently coupled to a glass carrier by means of an intermediate silane coupling agent, the silicon portion of the coupling agent being attached to the carrier while the organic portion of the coupling agent is coupled to the enzyme, the composition containing a metal oxide on the surface of the carrier disposed between the carrier and the silicon portion of the coupling agent. In U.S. Pat. No. 3,821,083 a water-insoluble polymer such as polyacrolein is deposited on an inorganic carrier and an enzyme is then covalently linked to the aldehyde groups of the polymer. However, according to most of the examples set forth in this patent, it is necessary to first hydrolyze the composite prior to the deposition of the enzyme on the polymer. Additionally the product which is obtained by the method of this patent suffers a number of disadvantages in that it first requires either the deposition, or initially the formation, of the desired polymer in an organic medium followed by its deposition on the inorganic carrier with a subsequent clean-up operation involving distillation to remove the organic medium. In addition to this, in another method set forth in this reference, an additional hydrolytic reaction is required in order to release the aldehyde groups from the initial acetal configuration in which they occurred in the polymer. Inasmuch as these aldehyde moieties are attached directly to the backbone of the polymer, the enzyme is also held adjacent to the surface of the polymer inasmuch as it is separated from the surface of the polymer by only one carbon atom of the reacting aldehyde group and, therefore, the enzyme is obviously subjected to the physico-chemical influences of the polymer as well as being relatively immobilized and inhibited from assuming its optimum configuration. Another prior art patent, namely, U.S. Pat. No. 3,705,084 discloses a macroporous enzyme reactor in which an enzyme is adsorbed on the polymeric surface of a macroporous reactor core and thereafter is cross-linked in place. By cross-linking the enzymes on the polymeric surface after adsorption thereof, the enzyme is further immobilized in part and cannot act freely as in its native state as a catalyst. The cross-linkage of enzymes in effect links them together, thereby preventing a free movement of the enzyme and decreases the mobility of the enzyme which is a necessary prerequisite for maximum activity.

U.S. Pat. No. 3,654,083 discloses a water-soluble enzyme conjugate which is prepared from an organic water-soluble support to which the enzyme is cross-linked and whose utility is limited only to cleaning compositions and pharmaceutical ointments. However, this enzyme composition also suffers from the disadvantages of the close proximity and interlocking of the enzyme and support, as well as the poor mechanical strength which is generally exhibited by enzyme conjugates based on organic polymeric supports.

U.S. Pat. No. 3,796,634 also discloses an immobilized biologically active enzyme which differs to a considerable degree from the immobilized enzyme conjugates of the present invention. The enzyme conjugate of this patent consists of an inorganic support comprising colloidal particles possessing a particle size of from 50 to 20,000 Angstroms with a polyethyleneimine, the latter being cross-linked with glutaraldehyde to staple the cross-linked polymer so formed as a monolayer on the surface of the colloidal particles, followed by adsorption of the enzyme directly onto this monolayer. Following this, the enzyme which is adsorbed as a monolayer on the surface of the colloidal particles is then cross-linked with additional glutaraldehyde to other adsorbed enzyme molecules to prevent them from being readily desorbed while in use. There is no indication of any covalent binding between enzyme and polymer matrix as is present in the present invention. By the enzyme molecules being cross-linked together on the surface of the support, this conjugate, therefore, is subjected to deactivation by both the cross-linking reaction and by the electronic and steric effects of the surface, said enzyme possessing limited mobility. Inasmuch as the product of this patent is colloidal in nature, it also possesses a very limited utility for scale-up to commercial operation, since it cannot be used in a continuous flow system such as a packed column because it would either be carried along and out of the system in the flowing liquid stream or, if a restraining membrane should be employed, the particles would soon become packed against the barrier to form an impervious layer. In addition, such a colloidal product could not readily be utilized in a fluidized bed apparatus, thereby limiting the chief utility to a batch type reactor such as a stirred tank type reactor from which it would have to be separated by centrifugation upon each use cycle. In contrast to this, the immobilized enzyme conjugates of the present invention may be employed in a wide variety of batch or continuous type reactors and therefore are much more versatile with regard to their modes of application.

In addition, another prior art reference U.S. Pat. No. 3,959,080 relates to a carrier matrix for immobilizing biochemical effective substances. However, the matrix which is produced according to this reference constitutes the product derived from the reaction of an organic polymer containing cross-linkable acid hydrazide or acid azide groups with a bifunctional cross-linking agent such as glutaraldehyde. However, this matrix also suffers from the relatively poor mechanical stability and other deficiencies which are characteristic of organic enzyme supports as well as the relatively complex organic reactions employed in preparing such polymeric hydrazides, etc.

As will hereinafter be shown in greater detail, the organic-inorganic matrix of the present invention will provide a support to which an enzyme may be covalently bound to provide a catalytic composite which will maintain its activity and stability over a relatively long period of use.

This invention relates to compositions of matter comprising support matrices for immobilized enzymes. More specifically, the invention is concerned with support matrices consisting of an organic-inorganic composite in which the inorganic support material is combined with an organic copolymer prepared in situ and substantially entrapped within the pores of the inorganic support. The copolymer is formed by the reaction of aminopolystyrene with a sufficient excess of a bifunctional monomer containing suitable reactive moieties to provide a copolymeric product containing terminally functionalized pendent groups capable of covalently binding enzymes at the terminal reactive portions thereof. In addition, the invention is also concerned with a process for preparing these matrices.

As hereinbefore set forth, the use of enzymes in analytical, medical or industrial applications may be greatly enhanced if said enzymes are in an immobilized condition, that is, said enzymes, by being in combination with other solids materials, are themselves in such a condition whereby they are not water soluble and therefore they may be subjected to repeated use while maintaining the catalytic activity of said enzyme. In order to be present in an immobilized state, the enzymes must be bound in some manner to a water insoluble carrier, thereby being commercially usable in an aqueous insoluble state.

It is therefore an object of this invention to provide novel compositions of matter in which enzymes may be covalently bound in an immobilized state.

A further object of this invention is to provide a process for preparing combined inorganic-organic support matrices which are utilized for covalently binding an enzyme to the functionalized pendent groups at the reactive terminal portions thereof.

In one aspect an embodiment of this invention resides in an organic-inorganic matrix comprising a porous, inorganic, water-insoluble solid support in combination with a copolymeric material resulting from the reaction of aminopolystyrene and a bifunctional monomer.

A further embodiment of this invention is found in a method for preparing an organic-inorganic matrix by depositing a salt of aminopoly-styrene on a solid support from an aqueous solution at a pH less than 7 and thereafter reacting the resultant aminopolystyrene-solid support composite with a bifunctional monomer to form the desired organic-inorganic matrix.

A specific embodiment of this invention is found in an organic-inorganic matrix which comprises gamma-alumina having combined therewith a copolymer resulting from the reaction of aminopolystyrene and an excess of glutaraldehyde.

Another specific embodiment of this invention is found in a process for preparing an organic-inorganic matrix which comprises depositing the hydrochloric acid salt of aminopolystyrene on gamma-alumina from an aqueous solution at a pH in the range of from about 1 to about 4, thereafter reacting the resultant aminopolystyrene-gamma-alumina composite with an excess of glutaraldehyde, and recovering the resultant organic-inorganic matrix.

Other objects and embodiments will be found in the following further detailed description of the present invention.

As hereinbefore set forth the present invention is concerned with support matrices which are used to immobilize enzymes, said matrices comprising an organic-inorganic composite consisting of an inorganic support material of the type hereinafter set forth in greater detail combined with a copolymeric organic material which, in the case of a porous support, is substantially entrapped in the pores of said porous support. The copolymeric composite will contain pendent groups extending therefrom, said pendent groups containing terminally positioned functional moieties which will enable an enzyme to be covalently bound to said group at the reactive terminal portions thereof. Furthermore, the invention is also concerned with a process for preparing these support matrices using relatively inexpensive reactants as well as utilizing more simple steps in the procedure for preparing said compositions. In addition, the mechanical strength and stability of enzyme conjugates which result from the covalent binding of enzymes to these support matrices will be greater than that which is possessed by the immobilized enzymes of the prior art. Therefore, it will be readily apparent that the compositions of matter of the present invention possesses economical advantages which are useful for industrial applications.

Examples of inorganic supports which may be utilized as one component of the support matrices of the present invention will consist of a wide variety of materials including porous supports such as alumina which possess pore diameters ranging from about 100 Angstroms up to about 55,000 Angstroms and which also possess an Apparent Bulk Density (ABD) in the range of from about 0.1 to about 0.6. The surface area of the particular inorganic porous support will also vary over a relatively wide range, said range being from about 1 to about 500 m$^2$/gm, the preferred range of surface area being from about 5 to about 400 m$^2$/gm. The configuration of the inorganic porous support material will vary, depending upon the particular type of support which is utilized. For example, the support material may be in spherical form, particulate form ranging from fine particles to macrospheres, as a ceramic monolith which may or may not be coated with a porous inorganic oxide, a membrane, ceramic fibers, alone or woven into a cloth, silica, mixtures of metallic oxides, sand particles, zeolites, mica, etc. The particle size may also vary over a wide range, again depending upon the particular type of support which is employed and also upon the substrate and the type of installation in which the enzyme conjugate is to be used. For example, if the support is in spherical form, the spheres may range in size from about 0.01" to about 0.25" in diameter, the preferred size ranging from about 1/32" to 1/8" in diameter. When the support is in particulate form, the particle size may also range between about the same limits. In terms of U.S. standard mesh sizes, such particles may range from about 2.5 to about 100 mesh, with about 10-40 mesh sizes preferred. Likewise, if the support is in the shape of ceramic fibers, the fibers may range from about 0.5 to about 20 microns in diameter or, if in the form of a membrane, the membrane may comprise a ceramic material which is cast into a thin sheet. It is to be understood that the aforementioned types of support configuration and size of the various supports are given merely for purposes of illustration, and it is not intended that the present invention be necessarily limited thereto.

It is also contemplated that the porous support materials may be coated with various oxides of the type hereinbefore set forth, or consist of mixtures thereof, or may have incorporated therein various other inorganic materials such as boron phosphate, etc., these inorganic materials imparting special properties to the support material. A particularly useful form of support will constitute a ceramic body which may have the type of porosity herein described for materials of the present invention or it may be honeycombed with connecting macro size channels throughout, such materials being commonly known as monoliths, and which may be coated with various types of porous alumina, zirconia, titanium oxide, etc. The use of such a type of support has the particular advantage of permitting the free flow of highly viscous substrates which are often encountered in commercial enzyme catalyzed reactions. One component of the organic portion of the support matrix comprises an aminopolystyrene which may be prepared by any manner known in the art and is deposited on the inorganic portion of the support material in a manner hereinafter set forth in greater detail. The composite is then treated with a bifunctional monomer to form the matrix upon which an enzyme may be immobilized. The bifunctional monomer reactant is present in sufficient excess as needed to produce pendent terminally functionalized groups, said bifunctional monomer being present in a range of from about 2 to about 50 moles or more relative to the reactive moieties of the support composite, the preferred range being from about 4 to about 25 moles of excess.

The functional groups which are present on the bifunctional monomer will comprise well-known reactive moieties capable of bonding readily with amino groups such as carbonyl, acyl, isocyanato, etc., moieties. As was also hereinbefore set forth, the reactive groups of the bifunctional compounds are preferably, but not necessarily, separated by chains containing from about 4 to about 10 carbon atoms. The reactive moieties of the bifunctional compounds are therefore capable of covalently bonding with both the aminopolystyrene component of the support matrix and subsequently, after washing out unreacted materials, also with the amino groups of the enzyme which is to be added in a subsequent step, said enzyme being then covalently bound to the reactive functional group at the terminal portion of the pendent chain. After addition of the enzyme to this composition, a relatively stable enzyme conjugate will be produced which possesses high activity and high stability. The unreacted enzyme can also be recovered for reuse. Due to the large excess of intermediate, or spacer bifunctional monomeric molecules which are used, the matrix will contain pendent groups comprising the spacer molecules, said molecules extending from the matrix and having reactive moieties available at the terminal portions thereof which are capable of reacting with and binding the enzyme to the aforesaid spacer molecules via covalent bonds. Therefore, it is readily apparent that a suitable organic-inorganic matrix which is applicable in binding enzymes will be formed, provided that a large enough excess of the bifunctional molecule is used to provide reactive pendent groups which are capable of subsequently reacting with the enzyme to be immobilized. By utilizing these functional pendent groups as a binding site for the enzymes, it will permit the enzymes to have a greater mobility and thus permit the catalytic activity of the enzyme to remain at a high level for a relatively longer period of time than will be attained when the enzyme has been immobilized by any of the other methods such as entrapment in a gel lattice, adsorption on a solid surface or cross-linkage of the enzyme with adjacent enzyme molecules by means of bifunctional reagents, etc. Not all formulations, however, will produce equivalent results in terms of stability or activity.

Examples of enzymes which may be immobilized by a covalent bonding reaction and which contain an amino group capable of reacting with an aldehydic, isocyanato, acyl, ester, etc., moiety of the pendent group which is attached to a polymeric material substantially entrapped in the pores of a porous support material will include trypsin, papain, hexokinase, betagalactosidase (lactase), ficin, bromelain, lactate dehydrogenase, glucoamylase, chymotrypsin, pronase, glucose, isomerase, acylase, invertase, amylase, glucose oxidase, pepsin, rennin, protease, xylanase, cellulase, etc. In general any enzyme whose active site is not involved in the covalent bonding can be used although not necessarily with equivalent results. While the aforementioned discussion was centered about pendent groups which contain as a functional moiety thereon an aldehydic or isocyanato group, it is also contemplated within the scope of this invention that the pendent group can contain functional moieties capable of reaction with carboxyl, sulfhydryl or other moieties usually present in enzymes. However, the covalent bonding of enzymes containing these other moieties with other pendent groups may not necessarily be effected with equivalent results and may also involve appreciably greater costs in preparing intermediates. It is to be understood that the aforementioned listing of porous solid supports, monomers, hydrolysates, polymers and enzymes are only representative of the various classes of compounds which may be used, and that the present invention is not necessarily limited thereto.

The preparation of the compositions of matter of the present invention is preferably effected in a batch type operation. In the preferred method of preparation, the inorganic support material will be treated with a solution, preferably aqueous in nature, of a salt of aminopolystyrene, the aqueous solution being maintained at a pH less than 7 and preferably in a range of from 1 to about 4. Examples of salts of aminopolystyrene which may be employed will include the hydrochloric acid salt, the sulfuric acid salt, the nitric acid salt, the phosphoric acid salt of aminopolystyrene, etc. The pH of the aqueous solution is maintained at the desired level by the addition of an acid such as those hereinbefore set forth, the amount of acid being added being sufficient, as hereinbefore set forth, to maintain the pH in a range of from 1 to about 4. Upon completion of the addition of the acid salt of the aminopolystyrene which in the preferred embodiment of the invention is effected at ambient temperature and atmospheric pressure, the mixture is placed under vacuum for a period of time which may range from about 0.5 up to about 4 hours or more in duration. Upon completion of the reaction time, the unadsorbed solution is removed and the treated support allowed to air dry until it is free flowing in nature. Thereafter the organic-inorganic composite is contacted with a sufficiently large excess of a bifunctional monomer of from about 3 to about 50 or more moles proportion relative to the amine content of the initial aminopolystyrene to provide pendent groups extending from the resultant copolymer, said pendent groups containing unreacted terminal functional moieties. The bifunctional monomer is also preferably added in an aqueous solution which, after reaction with the aminopolystyrene, is removed and the resultant matrix washed to separate any bifunctional monomer which may still be present.

As hereinbefore set forth, the use of an excess of the bifunctional monomer will result in pendent groups extending from the matrix which contain unreacted terminal functional moieties. The unreacted functional moieties are then available for covalent binding to the enzyme, which is added to the matrix, again usually in an aqueous solution. After removal of the unreacted materials by conventional means such as by treating, washing, etc., the enzyme which is covalently bound to the pendent functionalized groups remains attached at the terminal portions thereof. It is therefore readily apparent that the entire immobilized procedure can be conducted in a simple and inexpensive manner, for example, in a column packed with the inorganic supports, utilizing an aqueous or inexpensive solvent media. The procedure may be conducted over a temperature differential, if so desired, which may range from subambient (about 5° C.) up to about elevated temperatures of about 60° C., preferably at ambient (about 20°-25° C.) temperature, said procedure being effected by utilizing a minimal of operating steps and, in addition, permitting a ready recovery of the excess reactants, unbound enzyme and finished composition of matter, the excess reactants and unbound enzymes being available for reuse thereof.

It is also contemplated within the scope of this invention that the formation of the finished composition of matter may also be effected in a continuous manner of operation. When this type of operation is employed, a quantity of the solid support, either porous or non-porous in nature, is placed in an appropriate apparatus usually constituting a column. As in the case of the batch type operation, the solid support material may be in any form desired such as powder, pellets, monoliths, etc., and is charged to the column after which a preferably aqueous solution of a salt of aminopolystyrene is also charged and contacts the support until the latter is saturated with the solution. The aqueous solution is maintained at a pH less than 7 and preferably at a pH in a range of from about 1 to about 4 by the addition of an appropriate acid. After saturation of the support has been accomplished an excess is then drained and an intermediary spacer compound such as a reactive bifunctional monomer molecule, preferably in aqueous solution, is charged to the column, said bifunctional molecule being present in an excess in a range of from about 2 to about 50 moles or more relative to the amine content of the aminopolystyrene. While the formation of the matrix is effected during a period of time which may range from about 1 to about 10 hours or more in duration the formation is usually accomplished during a relatively short period of time. Following the completion of the desired residence time the excess spacer reactant such as glutaraldehyde is removed by draining followed by a thorough water washing to remove any unreacted materials.

To form an immobilized enzyme conjugate, an aqueous solution of an enzyme of the type hereinbefore set forth in greater detail is then passed through the column containing the thus formed support matrix thereby effecting a covalent bonding of the enzyme to the terminal reactive groups of the functionalized pendent moieties which extend from the matrix. This occurs until there is no further covalent binding of the enzyme to the pendent molecules. The excess enzyme is recovered in the effluent which is continuously withdrawn after draining and may be recycled to the column for further use. After washing the column, the column is then ready for use in chemical reactions in which the catalytic effect of the enzyme is to take place. These procedures are conducted within the time, temperature and concentration parameters hereinbefore set forth described in the batch type procedure and will result in comparable immobilized enzyme complexes. It is also contemplated within the scope of this invention that with suitable modifications of reaction parameters it will be obvious to those skilled in the art that the process may be applied to a wide variety of supports, bifunctional monomers and enzymes.

The following examples are given for purposes of illustrating the novel compositions of matter of the present invention and to the methods for preparing the same. However, it is to be understood that these examples are given merely for purposes of illustration and that the present invention is not necessarily limited thereto.

EXAMPLE I

In this example 1 gram of a porous alumina base having a particle size of from 25 to 40 mesh, an Apparent Bulk Density (ABD) of 0.34 and pore size ranging from 200 Angstroms to 10,000 Angstroms was admixed with 10 ml of a 5% weight by volume of aminopolystyrene having a molecular weight of 22,000 dissolved in aqueous 0.1 M hydrochloric acid. The two components were mixed at room temperature and allowed to stand for a period of 1 hour. At the end of this time the solution was degassed, filtered and the solid support containing the aminopolystyrene adsorbed thereon was dried. Following this, the composite was mixed with 10 ml of a 1.5% aqueous solution of glutaraldehyde which had a pH of 1.4 and maintained for a period of 1 hour at room temperature. At the end of this 1 hour period the excess glutaraldehyde was decanted and the organic-inorganic matrix was thoroughly washed with water several times. The final immobilized conjugate was then prepared by treating the matrix with 6482 units of a commercial glucoamylase sold under the Tradename "Ambazyme". The immobilization of the enzyme was effected during a period of 16 hours while maintaining the temperature of the composite at 4° C. by means of an ice bath. At the end of the 16 hour period the residual and unbound enzyme was washed out with water and a sodium chloride solution.

The immobilized enzyme conjugate was packed in a column and a 30% weight by volume solution of starch sold under the commercial Tradename "Maltrin-150" was passed over the beads while maintaining the temperature at 60° C., said starch feed being passed over the beads for a period of 2 hours at a flow rate of 2 ml/min. At the end of the 2 hour period, the amount of glucose formed was assayed. It was found that the activity of the enzyme conjugate was 3240 units/gram at the flow rate of 2 ml/min.; the unit being defined as the micromoles of glucose formed per minute per gram of immobilized enzyme conjugate.

EXAMPLE II

The above experiment was repeated with the exception that the enzyme, namely, glucoamylase was purified by means of an isopropanol precipitation procedure well known in the art, resulting in a 1.3 fold increase of purity of the enzyme. When this purified enzyme was immobilized in a manner similar to that set forth above and utilized to convert starch to glucose, it was found that the immobilized enzyme conjugate had an activity of 4070 units/gram at a flow rate of 2 ml/min.

EXAMPLE III

In a manner similar to that set forth in Example I above, 1 gram of an alumina base having a particle size of from 25–35 mesh and an ABD of 0.3 was added to 10 ml of a solution comprising 5% by volume of aminopolystyrene dissolved in aqueous 0.1 M hydrochloric acid. The mixture was maintained at room temperature for a period of 1 hour after which it was degassed, filtered and the aminopolystyrene-alumina matrix was dried. The dried beads were then added to 10 ml of a 1.5% aqueous solution of glutaraldehyde which had a pH of 1.4. The mixture was held for a period of 1 hour at room temperature and thereafter the excess glutaraldehyde was decanted. The organic-inorganic matrix was washed several times with water and thereafter was treated with 1300 units of glucose isomerase which had a specific activity of 8.5 units/mg of protein. The coupling was effected at a temperature of 4° C. for a period of 22 hours. The resulting immobilized glucose isomerase conjugate in which the enzyme was covalently bound to the free aldehyde functions of the copolymeric material which arose from the use of excess glutaraldehyde, was washed thoroughly with water and a 2 M aqueous sodium chloride solution to remove any unreacted enzyme.

The immobilized enzyme conjugate was packed in a suitable column and a 45% solution of fructose which possessed a pH of 8 and contained $5 \times 10^{-3}$ molar magnesium chloride was passed through the conjugate bed at a temperature of 60° C. for a period of 2 hours. The glucose and flow rate were assayed and it was found that this immobilized enzyme conjugate had an activity of 700 units/gram at a flow rate of 2 ml/min., with a coupling efficiency of 60%. It is further determined that the enzyme conjugate possessed a half-life of 22 days at 60° in a continuous column operation using the flow rate of 2 ml/min. of feed over the conjugate.

EXAMPLE IV

In this example an alumina base having a particle size of from 60–80 mesh and an ABD of 0.3 was treated with aminopolystyrene and an excess of glutaraldehyde in a manner similar to that set forth above to form an organic-inorganic support matrix. This support matrix was treated with glucose isomerase which possessed a specific activity of 15 units/mg. The coupling was effected by offering 2800 units of enzyme to the support matrix at a temperature of 4° C. for a period of 22 hours. After thorough washing of the immobilized enzyme conjugate, it was packed in a column and a fructose feed similar to that described in Example III above was passed through the conjugate bed for a period of 2 hours at a temperature of 60° C. The product was assayed and it was found that the immobilized enzyme conjugate had an activity of 1200 units/gram with a coupling efficiency of 54%.

We claim as our invention:

1. An organic-inorganic matrix having pendent covalent bonding sites for enzymatic conjugates which comprises a porous, water-insoluble, solid inorganic support containing a copolymeric material formed by the in situ reaction product of a water-soluble aminopolystyrene in an aqueous solution possessing a pH of less than 7.0 and a bifunctional monomer selected from the group consisting of organic compounds containing carbonyl, acyl and isocyanato moieties, wherein said bifunctional monomer is added in a molar excess of 2 to 50 moles of monomer per mol of the amine content of said water-soluble aminopolystyrene.

2. The matrix as set forth in claim 1 in which said solid support comprises a metallic oxide.

3. The matrix as set forth in claim 2 in which said metallic oxide is an alumina.

4. The matrix as set forth in claim 3 in which said alumina is gamma-alumina.

5. The matrix as set forth in claim 1 in which said solid support is a ceramic monolith coated with a porous metallic oxide.

6. The matrix as set forth in claim 1 in which said solid support is a porous silica.

7. The matrix as set forth in claim 1 in which the bifunctional monomer is glutaraldehyde.

8. The organic-inorganic matrix as set forth in claim 1 which is prepared by depositing a water soluble salt of aminopolystyrene on a solid support from an aqueous solution at a pH less than 7 and thereafter reacting the resultant aminopolystyrene-solid support composite with said bifunctional monomer to form the desired organic-inorganic matrix.

9. The matrix as set forth in claim 8 in which the pH is in a range of from about 1 to about 4.

10. The matrix as set forth in claim 8 in which said water soluble salt of aminopolystyrene is the hydrochloric acid salt.

11. The matrix as set forth in claim 8 in which said water soluble salt of aminopolystyrene is sulfuric acid salt.

12. The matrix as set forth in claim 8 in which the bifunctional monomer is glutaraldehyde.

* * * * *